United States Patent

Ogino et al.

[11] Patent Number: 5,484,588
[45] Date of Patent: Jan. 16, 1996

[54] ATTRACTING AND INGESTION-STIMULATING AGENT FOR COCKROACH

[75] Inventors: Kazumasa Ogino, Ageo; Haruo Shimamura, Yono; Kazuyuki Tomisawa, Ina; Fumio Urushizaki, Ageo; Masami Nemoto, Okegawa; Tuguchika Yoshida, Ageo, all of Japan

[73] Assignee: Taisho Pharmaceutical, Co., Ltd., Tokyo, Japan

[21] Appl. No.: 965,289
[22] PCT Filed: Aug. 8, 1991
[86] PCT No.: PCT/JP91/01059
 § 371 Date: Feb. 2, 1993
 § 102(e) Date: Feb. 2, 1993
[87] PCT Pub. No.: WO92/02134
 PCT Pub. Date: Feb. 20, 1992

[30] Foreign Application Priority Data

Aug. 9, 1990 [JP] Japan .................... 2-210680

[51] Int. Cl.$^6$ ............... A01N 33/04; A01N 33/06
[52] U.S. Cl. ............... 424/84; 514/655; 514/657
[58] Field of Search ............... 514/655, 657; 424/84

[56] References Cited

U.S. PATENT DOCUMENTS

| | | | |
|---|---|---|---|
| 2,582,375 | 1/1952 | Englert et al. | 514/657 |
| 4,627,981 | 12/1986 | Shimano et al. | 424/84 |
| 4,911,907 | 3/1990 | Shimamura et al. | 421/84 |

OTHER PUBLICATIONS

Chemical Abstracts, vol 68, No. 23, Jun. 3, 1968, AN–104942d, V. Grinsteins, et al., "Synthesis and Study of Potential Antidepressants. Synthesis and Biochemical Study of Omega–Aminomethyl Derivatives of Condensed Aromatic and Heterocyclic Compounds".

Chemical Abstracts, vol. 66, No. 13, Mar. 27, 1967, AN–54916j, J. Kloubek, "Effect of Structure of Organic Substances on Lyophobicity. Properties of Aminotetrahydronaphthalenes and Their N–Methyl Homologs".

The Steric Effect of Methylene Groups. VII, by Stuart W. Fenton, Arthur E. DeWald and R. T. Arnold, Feb. 20, 1955.

Possible Antituberculosis Compounds. Part VII: Preparation of a– and B–Tetrahydronaphthylamidines, Journal Indian Chem. Soc., vol. 36, No. 11, 1959.

Synthesis and Study of Potential Antidepressants. Synthesis and biochemical study of w–aminomethyl derivatives of condensed aromatic and heterocyclic compounds. V. Grinsteins, I. Vina, and M. Meldraja. Latv. PSR Zinat. Akad. Vesis 1967(7), 128–36(Russ). With English Abstract.

*Primary Examiner*—Allen J. Robinson
*Assistant Examiner*—B. Bembenick
*Attorney, Agent, or Firm*—Oblon, Spivak, McClelland, Maier & Neustadt

[57] ABSTRACT

There are provided attracting and ingestion-stimulating agents for cockroach comprising as the active ingredient one or more compounds represented by the formula

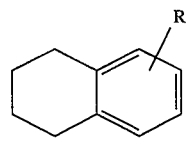

wherein R represents an amino group or an aminomethyl group.

The attracting and ingestion-stimulating agents for cockroach exhibit a very potent attracting and ingestion-stimulating activity in the known species of house cockroach, both male and female.

2 Claims, No Drawings

ATTRACTING AND INGESTION-STIMULATING AGENT FOR COCKROACH

TECHNICAL FIELD

The present invention relates to attracting and ingestion-stimulating agents for cockroaches.

BACKGROUND ART

Cockroach is one of the sanitarily harmful insects most widely known throughout the world. As the house cockroach are known *Periplaneta fuliginosa* L., *P. japonica* K., *P. americana* L., *Blattella germanica* L., *Blatta orientalis* L., etc.

In general, it is important for extermination of cockroach to possess both an attracting activity and an ingestion-stimulating activity. We have already provided several cockroach attracting and ingestion-stimulating agents which simultaneously possess the activities both [U.S. Pat. Nos. 4,627,981; 4,911,907].

Tetralol, naphthol and phenol compounds and Iris tectoramines alcohols, which are active ingredients of these cockroach attracting and ingestion-stimulating agents, are sufficiently active: without any additives. However, they are often active against male *P. americana* L. only and, when applied to colonies of other species of cockroach or colonies of female cockroach only, they sometimes produce lower effects.

DISCLOSURE OF THE INVENTION

In order to cover the defects of the prior art attracting and ingestion-stimulating agents for cockroach and to provide more effective ones, we have investigated a variety of tetralin compounds, naphthalene compounds, benzene compounds and other heterocyclic compounds for their cockroach attracting and ingestion-stimulating activities. As a result of extensive studies on bicyclic nitrogen-containing compounds as set forth below in Test Example 1, we have found that specific tetralin compounds exhibit a high attracting and ingestion-stimulating action in adult *P. americana* L. and further that they have both an attracting and an ingestion-stimulating actions which are highly active against many species of cockroach, and that the activity does not go down even when male and female cockroaches live together.

This invention is directed to attracting and ingestion-stimulating agents for cockroach comprising as an active ingredient one or more compounds represented by the formula

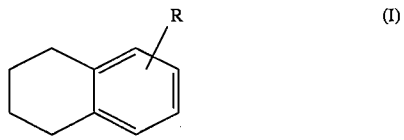

(I)

wherein R represents an amino group or an aminomethyl group.

The compounds represented by the formula I are known compounds disclosed, for example, in the literatures cited below. However, none of these compounds are known for their cockroach attracting and ingestion-stimulating activities:

V. Grinsteins et al., Latv. RSR Zinat. Akad. Vestis, Kim. Ser., 1967, 7, 128

V. S. Misra et al., J. Indian Chem. Soc., 1959, 36, 803

S. W. Fenton et al., J. Am. Chem. Soc., 1955, 77, 979

Attracting and ingestion-stimulating agents for cockroach according to the invention can be prepared, for example, by dissolving an active compound in an appropriate solvent (for example, a hydrophilic organic solvent such as acetone, methanol, ethanol, tetrahydrofuran, ethylene glycol, diethylene glycol or N, N-dimethylformamide, or a lipophilic organic solvent such as benzene, chloroform, ether, methylene chloride or n-hexane), then impregnating an appropriate carrier (for example paper, cardboard, non-woven cloth, cotton cloth or flannel) with the solution and drying off the solvent to provide attracting tapes or the like. The active compounds according to the invention can also be formulated into a form such as granules, pills or tablets by a conventional method (e.g., methods in Japanese Pharmacopoeia, Revised Ed. XII) with the aid of usual binders, excipients, lubricants, stabilizers and others. These cockroach attracting and ingestion-stimulating agents can be used for exterminating cockroach, for example, by mounting the agent on a receptacle-shaped cockroach trap at a center of its tackiness plate.

Alternatively, attracting and ingestion-stimulating agents for the cockroach of the invention may be prepared in such a form as attracting tackiness plate, or attracting and insecticidal sheet, plate or tape by blending an active compound according to the invention in a tackifier or a resin, or incorporating it together with an insecticidal component into a tackifier or a resin. They may also be formulated together with an insecticidal component and conventional emulsifier, dispersant, penetrating agent, suspending agent, wetting agent, spreading agent or excipient into a formulation such as emulsions, wettable powders, granules, powders, oily liquids, or a formulation according to Guidelines for the Preparation of Pharmaceuticals (1990) such as mats, balls, pastes, baits or granules for use as an attracting insecticide.

The active ingredients according to the invention exert an attracting and ingestion-stimulating activity in a very small amount so that no particular care should be taken for the amount to be used. It is preferable, for example, that a bait usually contains the active ingredient in a concentration of 0.01% by weight or more of the whole amount.

The attracting and ingestion-stimulating action of the agents according to the invention will be described below in detail with reference to test examples.

Test Example 1

(Test material)

The compounds used are shown in Table 1.

(Test insect)

A group of *P. americana* L. consists of 200 adult male and female (1:1) cockroaches. Three groups were 10 prepared per one test material.

(Test method)

On a filter paper (Toyo Filter Paper No. 1) 11 cm in diameter were drawn 6 circles each 2 cm in diameter at an equal distances. Five of the circles respectively were applied with 10 μl of an acetone solution containing 1 mg of a test or control material, and the remaining circle with 10 μl of acetone as blank. The filter paper was thoroughly dried in air to evaporate the solvent. There was thus prepared a test sheet.

Each group of the test insects was housed in a separate cage (transparent polycarbonate vessel 35×30×18 cm in size) and was reared under conditions of 25° C. and 12L–12D (12-hour light period and 12-hour dark period) for fitting the insects in the cage. The test sheets prepared in various combinations were each placed in the cage. After 24 flours, the test sheets were recovered and examined for the degree of ingestion. The test was repeated three times for each of the test materials. The cage once used in a test was employed for a subsequent test at an interval of one week or longer.

(Method of evaluation)

The tested filter paper was evaluated on the following 7 grades of score:

−: No mark of eating observed

±: One to several marks of eating observed

1: 10–20 marks of eating observed

2: Marks of eating observed on a half or more part of the applied area

3: Marks of eating observed almost throughout the applied area or marks of vigorous eating to perforate observed 4: The applied area almost entirely perforated 5: The applied area entirely bitten off (Results)

The results are shown in Table 1.

TABLE 1

| Name | Score |
|---|---|
| 1-Amino-5,6,7,8-tetrahydronaphthalene | 5 |
| 1-Amino-4-bromo-5,6,7,8-tetrahydronaphthalene | 4 |
| 1-Amino-2,4-dibromo-5,6,7,8-tetrahydronaphthalene | 1 |
| 1-Amino-2,4-dibromo-5,6,7,8-tetrahydronaphthalene hydrobromide | − |
| 1-Amino-1,2,3,4-tetrahydronaphthalene | 3 |
| 1-Amino-1,2,3,4-tetrahydronaphthalene hydrochloride | − |
| 1,2,3,4-Tetrahydronaphthalene-7-amide | − |
| 1-Ethylamino-5,6,7,8-tetrahydronaphthalene | 1 |
| 1-Acetylamino-5,6,7,8-tetrahydronaphthalene | − |
| 1-Acetylamino-4-bromo-5,6,7,8-tetrahydronaphthalene | − |
| 1-Trifluoroacetylamino-5,6,7,8-tetrahydronaphthalene | − |
| N-Methyl-1-trifluoroacetylamino-5,6,7,8-tetrahydronaphthalene | − |
| N-Butyl-1-trifluoroacetylamino-5,6,7,8-tetrahydronaphthalene | 1 |
| 2-Amino-5,6,7,8-tetrahydronaphthalene | 5 |
| 2-Amino-5,6,7,8-tetrahydronaphthalene hydrochloride | 4 |
| 2-Aminomethyl-5,6,7,8-tetrahydronaphthalene | 5 |
| 2-Aminomethyl-5,6,7,8-tetrahydronaphthalene hydrocarbonate | 5 |
| 1-Amino-4-chloronaphthalene | 2 |
| 1-Amino-2-naphthol hydrochloride | − |
| 1-Bromo-2-aminonaphthalene | ± |
| N-Ethyl-1-naphthylamine | 1 |
| 1-Acetylaminonaphthalene | − |
| α-Naphthylurea | − |
| 1-(1-Naphthyl)-2-thiourea | − |
| N-Ethyl-1-naphthylamine hydrobromide | ± |
| 2-Amino-4-methoxy-naphthalene | 2 |
| 1-Anilinonaphthalene | − |
| 1-Amino-2-bromo-4-nitronaphthalene | + |
| 8-Amino-2-naphthol | − |
| 2-Aminomethylnaphthalene | 2 |
| 1-Naphthalenemethylamine | ± |
| N-Methyl-1-naphthylmethylamine | 2 |
| DL-1-(Naphthyl)methylamine | 2 |
| Quinoline | − |
| Isoquinoline | 2 |
| Quinoxaline | − |
| Cinnoline | − |
| 5,6,7,8-Tetrahydroquinoline | ± |
| 5,6,7,8-Tetrahydroisoquinoline | 2 |
| 2-Methylquinoline | 1 |
| 8-Methylquinoline | 1 |
| 2-Methyl-4-aminoquinoline | ± |
| 2-Methyl-6-aminoquinoline | − |
| 2-Methyl-8-aminoquinoline | 1 |
| 2-Methyl-1,2,3,4-tetrahydroquinoline | 1 |

TABLE 1-continued

| Name | Score |
|---|---|
| 3-Methyl-5,6,7,8-tetrahydroquinoline | 5 |
| 3-Methylquinoline | 4 |
| 1-Methylisoquinoline | 5 |
| 2,4-Dimethylquinoline | 4 |
| 5-Aminoindan | 2 |
| 3,4-(Methylenedioxy)aniline | 2 |
| 2-Amino-9-hydroxyfluorene | − |

Test Example 2

(Test material)

The compounds used as test materials are shown in Table 2. As controls were used 5,6,7,8-tetrahydro-1-naphthol, 5,6,7,8-tetrahydro-2-naphthol, 1-naphthol, 2-naphthol and p-n-amylphenol.

(Test insect)

Groups of adult male, adult female, larva male and larva female P. americana L. each consisting of 200 cockroaches of single sex and instar and a group of 200 P. americana L. cockroaches of varied sexes and instars consisting of each 50 of adult male, adult female, larva male and larva female cockroaches (called male/female mixed group hereinbelow) were prepared. (The adult as referred to is the insect of one-month old after adult emergence, and the larva is the middle instar insect of four-month old after hatching.)

(Test method)

The method of treatment in Test Example 1 was followed, and the degree of ingestion was examined for the single sex and instar groups and the male/female mixed group of P. americana L., respectively.

(Method of evaluation)

The method of evaluation was the same as in Test Example 1.

(Results)

The results are shown in Table 2.

TABLE 2

| Compound name | Adult male | Adult female | Larva male | Larva female | Mixed |
|---|---|---|---|---|---|
| 1-Amino-5,6,7,8-tetrahydronaphthalene | 3 | 5 | 3 | 4 | 5 |
| 1-Amino-4-bromo-5,6,7,8-tetrahydronaphthalene | 3 | 4 | 3 | 3 | 4 |
| 2-Amino-5,6,7,8-tetrahydronaphthalene | 4 | 5 | 4 | 4 | 5 |
| 2-Amino-5,6,7,8-tetrahydronaphthalene hydrochloride | 3 | 4 | 3 | 3 | 4 |
| 2-Aminomethyl-5,6,7,8-tetrahydronaphthalene | 4 | 5 | 4 | 4 | 5 |
| 2-Aminomethyl-5,6,7,8-tetrahydronaphthalene hydrocarbonate | 4 | 5 | 4 | 4 | 5 |
| 3-Methyl-5,6,7,8-tetrahydroquinoline | 3 | 5 | 3 | 4 | 5 |
| 3-Methylquinoline | 3 | 4 | 3 | 3 | 4 |
| 1-Methylisoquinoline | 4 | 5 | 3 | 4 | 5 |
| 2,4-Dimethylquinoline | 3 | 4 | 3 | 4 | 4 |
| 5,6,7,8-Tetrahydro-1-naphthol | 4 | ± | 4 | − | 4 |
| 5,6,7,8-Tetrahydro-2-naphthol | 4 | ± | 5 | − | 4 |
| 1-Naphthol | 2 | − | 2 | − | 2 |
| 2-Naphtol | 2 | − | 2 | − | 2 |

TABLE 2-continued

| Compound name | Adult male | Adult female | Larva male | Larva female | Mixed |
|---|---|---|---|---|---|
| p-n-Amylphenol | 5 | 2 | 5 | 1 | 5 |
| Blank (acetone) | – | – | – | – | – |

Table 2

It was thus demonstrated that 1-amino-5,6,7,8-tetrahydronaphthalene, 2-amino-5,6,7,8-tetrahydronaphthalene and 2-aminomethyl-5,6,7,8-tetrahydronaphthalene compounds and salts thereof induce a much stronger ingestion response in any of the groups than do the control compounds. In addition, whereas the control compounds were highly active in male only, the compounds used as test material were active in female, too.

Test Example 3

(Test material)

The compounds listed in Table 3 were used as test materials. As controls were used 5,6,7,8-tetrahydro-1-naphthol, 5,6,7,8-tetrahydro-2-naphthol, 1-naphthol, p-n-amylphenol and p-n-amylaniline.

(Test insect)

Groups of P. fuliginosa S., P. japonica K., P. australasiae L., B. orientalis L. and B. germanica L., each consisting of 200 adult male and female (1:1) cockroaches of one-month old after adult emergence were used. Five groups were prepared for each species.

(Test method)

The method of treatment in Test Example 1 was followed, and the degree of ingestion was examined for each of the cockroach species.

(Method of evaluation)

Appearance of the filter papers after the test was evaluated on the following 5 grades of score:

−: No mark of eating observed

±: One to several marks of eating observed

1: 10–20 marks of eating observed

2: Marks of eating observed on a half or more part of the applied area

3: Marks of eating observed almost throughout the applied area (Results)

The test materials exerted a potent attracting and ingestion-stimulating action in the varied species of cockroach. On the other hand, the control compounds, 5,6,7,8-tetrahydro-1-naphthol, 5,6,7,8-tetrahydro-2-naphthol, 1-napthol, p-n-amylphenol and p-n-amylaniline had a weaker activity than that of the test materials.

The results are shown in Table 3.

TABLE 3

| | Species of cockroach | | | | |
|---|---|---|---|---|---|
| Compound name | P. fliginosa S. | B. orientalis L. | P. japonica K. | P. australasiae L. | B. germanica L. |
| 1-Amino-5,6,7,8-tetrahydronaphthalene | 2 | 1 | 2 | 3 | 1 |
| 2-Amino-5,6,7,8-tetrahydronaphthalene | 2 | 2 | 2 | 3 | 1 |
| 2-Aminomethyl-5,6,7,8-tetrahydronaphthalene | 3 | 2 | 2 | 3 | 2 |
| 5,6,7,8-Tetrahydro-1-naphthol | – | – | – | – | – |
| 5,6,7,8-Tetrahydro-2-naphthol | – | – | – | – | – |
| 1-Naphthol | – | – | – | – | – |
| p-n-Amylphenol | 1 | 1 | 1 | 2 | 1 |
| p-n-Amylaniline | 1 | ± | 1 | 1 | 1 |
| Blank (acetone) | – | ± | – | – | – |

Test Example 4

(Test material)

2-Amino-5,6,7,8-tetrahydronaphthalene or 2-aminomethyl-5,6,7,8-tetrahydronaphthalene was used.

(Test insect)

Groups of P. americana L., P. fuliginosa S., P. japonica K., B. germanica L. and B. orientalis L., 3 groups for each species, 15 groups in total, each group consisting of 50 adults and 50 larvae were prepared.

(Test method)

An attractant was prepared by applying a solvent containing 1000 μg of a test material to a circular filter paper (Toyo Filter Paper No. 1) 1 cm in diameter. Separately, a mixture of 75 parts of powdery fish meal, 5 parts of maltose, 5 parts of L-arabinose, 5 parts of oleic acid and 10 parts of rice bran oil was kneaded together with some water, and the mixture was formed into a small granular attractant weighing about 0.7 g per granule.

Five rooms, approximately 6 mats in size, were used. One week before initiation of the test each room was stocked with a group of different species of the cockroach, which was given bait and water ad lib.

A set of trap A which is the cockroach trap described in Japanese Utility Model Application Laid-Open-to-Public No. 142679/1979 width the above-prepared circular attractant mounted on the tacky surface at the center, trap B with the above-prepared granular bait attractant (0.7 g) mounted on the tacky surface at the center as in trap A and trap C with nothing mounted on the tacky surface was placed in the room. After 24 hours the number of the cockroaches trapped in each of the traps was counted.

The experiment was repeated three times, and the mean value, rounded to the nearest whole number, was taken as the number of the trapped cockroaches.
(Method of evaluation)
Effect of the attractants was evaluated on the basis of the number of cockroaches trapped in traps A, B and C, respectively.
(Results)
2-Amino-5,6,7,8-tetrahydronaphthalene and 2-aminomethyl-5,6,7,8-tetrahydronaphthalene were found to be useful with their high attracting effects also when used in the trap.
The results are shown in Table 4 and Table 5.

TABLE 4

(Test material: 2-Amino-5,6,7,8-tetrahydronaphthalene)

| Species | Number of trapped cockroaches | | |
|---|---|---|---|
| | Trap A | Trap B | Trap C |
| P. americana L. | 54 | 26 | 12 |
| P. fuliginosa S. | 50 | 23 | 10 |
| P. japonica K. | 52 | 20 | 15 |
| B. germanica L. | 54 | 28 | 14 |
| B. orientalis L. | 58 | 21 | 11 |

TABLE 5

(Test material: 2-Aminomethyl-5,6,7,8-tetrahydronaphthalene)

| Species | Number of trapped cockroaches | | |
|---|---|---|---|
| | Trap A | Trap B | Trap C |
| P. americana L. | 58 | 23 | 7 |
| P. fuliginosa S. | 53 | 19 | 11 |
| P. japonica K. | 56 | 22 | 12 |
| B. germanica | 61 | 23 | 10 |
| B. orientalis | 68 | 19 | 9 |

Best Mode for Carrying Out the Invention

The attracting and ingestion-stimulating agents of the invention will be described below in detail with reference to examples.

EXAMPLE 1

A mixture of 75 parts of powdery fish meal, 5 parts of maltose, 5 parts of L-arabinose, 5 parts of oleic acid, 10 parts of rice bran oil, 0.06 part of sodium benzoate, 0.02 part of dibutylhydroxytoluene, 1 part of permethrin, 0.05 part of 2-aminomethyl-5,6,7,8-tetrahydronaphthalene and 0.03 part of p-n-amylphenol was kneaded together with some water, and the mixture was formed into a small granular cockroach-attracting toxic bait of the invention weighing about 0.7 g per granule.

EXAMPLE 2

150 parts of soluble starch, 150 parts of potato starch, 100 parts of boric acid, 0.6 part of sodium benzoate, 0.2 part of dibutylhydroxytoluene, 0.03 part of 2-amino-5,6,7,8-tetrahydronaphthalene, 0.1 part of p-n-amylphenol and 599.5 parts of water were blended and formed into a cockroach-attractant toxic bait of the invention weighing about 10 g per piece.

EXAMPLE 3

10 parts of wheat powders, 35 parts of soluble starch, 35 parts of starch, 1 part of methoprene, 0.06 part of sodium benzoate, 0.02 part of dibutylhydroxytoluene, 0.05 part of p-n-butylphenol and 0.03 part of 2-amino-5,6,7,8-tetrahydronaphthalene hydrochloride were blended together with an appropriate amount of water and formed into pieces weighing about 5 g per piece followed by drying to give a cockroach-attractant toxic bait of the invention.

EXAMPLE 4

100 parts of corn syrup, 30 parts of sorbitol, 14 parts of gelatin, 48 parts of water, 2 parts of pyriproxyfen, 0.06 part of sodium benzoate, 0.02 part of dibutylhydroxytoluene, 0.05 part of p-n-butylphenol and 0.1 part of 2-aminomethyl-5,6,7,8-tetrahydronaphthalene hydrocarbonate were blended and formed into a cockroach-attractant toxic bait of the invention weighing about 10 g per piece.

EXAMPLE 5

40 parts of thick malt syrup, 45 parts of oats powders, 11 parts of macrogol, 0.5 part of cyphenothrin, 1 part of diflubenzuron, 0.06 part of sodium benzoate, 0.02 part of dibutylhydroxytoluene and 0.1 part of 2-amino-5,6,7,8-tetrahydronaphthalene hydrochloride were blended and formed into a cockroach-attractant toxic bait of the invention weighing about 10 g per piece.

EXAMPLE 6

20 parts of brown sugar, 2 parts of corn oil, 2 parts of chrysalis powders, 20 parts of biscuit powders, 50 parts of dextrin, 0.06 part of sodium benzoate, 0.02 part of dibutylhydroxytoluene, 2 parts of hydramethylnon, 0.03 part of 2-aminomethyl-5,6,7,8-tetrahydronaphthalene and 0.02 part of p-n-amylphenol were blended and formed into a cockroach-attractant toxic bait of the invention weighing about 5 g per piece.

EXAMPLE 7

20 parts of powdery sugar, 10 parts of corn oil, 30 parts of sweet corn oil, 60 parts of crystalline cellulose, 2 parts of ethofenprox, 0.06 part of sodium benzoate, 0.02 part of dibutylhydroxytoluene, 0.03 part of 2-amino-5,6,7,8-tetrahydronaphthalene and 0.03 part of p-tert-amylphenol were blended and formed into a cockroach-attractant toxic bait weighing about 5 g per piece.

EXAMPLE 8

15 parts of mineral oil, 2 parts of ammonium hydroxide, 2 parts of polyoxyethylene nonylphenyl ether, 0.5 part of carboxymethyl cellulose, 3.5 parts of potato starch, 1 part of propoxur, 0.5 part of fenoxycarb, 0.06 part of sodium benzoate, 0.02 part of dibutylhydroxytoluene, 0.05 part of p-sec-butylphenol, 0.03 part of 2-aminomethyl-5,6,7,8-tetrahydronaphthalene and 60.7 parts of water were blended and formed into a cockroach-attractant toxic bait of the invention weighing about 5 g per piece.

EXAMPLE 9

15 parts of white mineral oil, 1.5 parts of polyoxyethylene glycol dioleate, 2 parts of polyoxyethylene nonylphenyl ether, 1 part of hydroxyethyl cellulose, 0.5 part of xanthane gum, 5 parts of corn starch, 2 parts of chloropyrifos-methyl, 0.06 part of sodium benzoate, 0.02 part of dibutylhydroxytoluene, 0.05 part of 3-methyl-4-isopropylphenol and 0.05 part of 2-aminomethyl-5,6,7,8-tetrahydronapthalene hydrocarbonate were blended and formed into a cockroach-attractant toxic bait of the invention weighing about 5 g per piece.

EXAMPLE 10

To about 1 g of 2-aminomethyl-5,6,7,8-tetrahydronaphthalene was added about 200 ml of n-hexane, and the mixture was thoroughly stirred using a stirrer for about 10 min. The resulting solution was uniformly moistened using a distributor in a woven cloth 20 cm in 10 width, 50 cm in length and 0.1 cm in thickness followed by drying in air sufficiently well to evaporate the n-hexane. The moistened cloth was cut to pieces 0.5 cm in width and 20 cm in length to prepare attractant and ingestion-stimulant tapes. The tapes can be mounted on a receptacle-shaped cockroach trap at a center of its tackiness plate.

EXAMPLE 11

0.5 g of 2-aminomethyl-5,6,7,8-tetrahydronaphthalene hydrochloride, 100 g of boric acid, 150 g of soluble starch, 150 g of potato starch and 599.5 g of water were blended and formed into baits of an appropriate size.

EXAMPLE 12

0.05 g of 2-amino-5,6,7,8-tetrahydronaphthalene, 20 g of white petrolatum and 77. 95 g of d-phenothrin were blended and coated on a polyethylene tape 5 cm in width and 200 m in length, which was then cut to prepare insecticidal tapes 5 cm in width and 20 cm in length.

EXAMPLE 13

To 200 ml of acetone was added 0.5 g of 2 -aminomethyl-5,6,7,8- tetrahydronaphthalene, and the mixture was thoroughly stirred to give a solution. A circular filter paper (Toyo Filter Paper No. 2) 3 cm in diameter was moistened using a pipette with about 0.1 ml of the solution, and the filter paper was then dried in air to completely evaporate the acetone. A piece of the moistened filter 10 paper was placed in a glass cylinder (13 cm in diameter and 18 cm in height) interiorly coated with petrolatum to prepare a simple cockroach trap.

EXAMPLE 14

0.5 g of 2-aminomethyl-5,6,7,8-tetrahydronaphthalene, 0.5 g of p-n-amylphenol, 200 g of natural rubber, 780 g of ARCON (Trade name: Manufactured by Arakawa Kagaku Kogyo K.K.) and 10 g of dibutylhydroxytoluene were; thoroughly kneaded and coated using a roller on a cardboard 9 cm in width and 20 cm in length to prepare a tackiness plate for the receptacle-shaped cockroach trap.

EXAMPLE 15

0.5 g of 2-aminomethyl-5,6,7,8-tetrahydronaphthalene, 50 g of hydramethylnon, 200 g of soluble starch, 150 g of potato starch and 599.5 g of water were blended and formed into baits of an appropriate size.

Industrial Applicability

The attracting and ingestion-stimulating agents of the invention not only exhibit a potent attracting and ingestion-stimulating activity on various species of cockroach but also are highly effective in cockroach extermination even where male and female cockroaches live together.

The attracting and ingestion-stimulating component of the invention, even when used alone, shows a strong attracting and ingestion-stimulating effect to cockroach and furthermore possesses a good stationing effect. In preparing an attracting and ingestion-stimulating agent no additives such as starch and sugars are needed. This brings about low production cost and minimize the size of the preparation for easiness on use. The attracting and ingestion-stimulating component for cockroaches according to the invention can also provide each of the cockroach controlling agents with fast-acting property.

What is claimed is:

1. A method of attracting and ingestion-stimulating cockroaches comprising applying, to a location wherein cockroaches are present in the environment, a composition for attraction and ingestion-stimulation of said cockroaches wherein said composition comprises from 0.01% to 0.25% by weight of one or more compounds represented by the formula

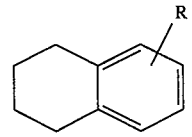

wherein R represents an amino group or an aminomethyl group whereby said cockroaches are attracted to said one or more compounds.

2. The method of claim 1, wherein said composition is applied in a trap for cockroaches.

* * * * *